United States Patent
Spivack

[11] 4,182,704
[45] Jan. 8, 1980

[54] HINDERED PHENYL PHOSPHITES

[75] Inventor: John D. Spivack, Spring Valley, N.Y.

[73] Assignee: Ciba-Geigy Corporation, Ardsley, N.Y.

[21] Appl. No.: 904,064

[22] Filed: May 8, 1978

Related U.S. Application Data

[62] Division of Ser. No. 710,063, Jul. 30, 1976, Pat. No. 4,094,855.

[51] Int. Cl.$^2$ .......................... C07F 9/145; C08K 5/52
[52] U.S. Cl. .............................. 260/45.8 NT; 260/403; 260/935
[58] Field of Search .......... 260/935, 45.8 NT, 45.8 R, 260/45.85 R, 45.85 B, 45.9 HA, 45.95 C, 45.95 H

[56] References Cited

U.S. PATENT DOCUMENTS

| | | | |
|---|---|---|---|
| 2,617,793 | 11/1952 | Young | 260/935 X |
| 4,094,855 | 6/1978 | Spivack | 260/935 X |

Primary Examiner—Anton H. Sutto
Attorney, Agent, or Firm—Vincent J. Cavalieri

[57] ABSTRACT

Compounds of the formula

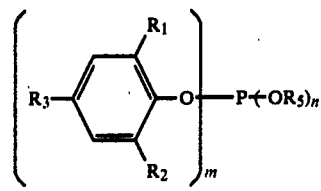

wherein
  $R_1$ and $R_2$ are independently lower alkyl or hydrogen, provided that only one of $R_1$ and $R_2$ is hydrogen,
  $R_3$ is —(A)—COOR$_4$ or CN where
  A is alkylene of 1 to 24 carbon atoms,
  $R_4$ is alkyl of 1 to 24 carbon atoms, phenyl or alkyl substituted phenyl
  q is 0 or 1
  m and n are each 1 or 2, the values of m and n being such that the trivalent state of is satisfied, and
  $R_5$ is alkanoyl, benzoyl, or alkyl substituted benzoyl,
are suitable for stabilizing organic material against thermal, oxidative and ultraviolet light degradation.

15 Claims, No Drawings

HINDERED PHENYL PHOSPHITES

This is a divisional of application Ser. No. 710,063, filed on July 30, 1976, now U.S. Pat. No. 4,094,855 which was issued on June 13, 1978.

BACKGROUND OF THE INVENTION

The prior art discloses many materials which stabilize organic materials against deterioration. For example, many varieties of compounds are known which inhibit the discoloration of polymers on exposure to heat and light. Such protection is necessary because most organic polymers, especially polyolefins such as polyethylene or polypropylene, which are used for manufacturing articles tend to develop color with passage of time. The discoloration may be due to various factors such as the decomposition of the polymer, the antioxidant or to the presence of residual metal catalyst or residual peroxides used to control polymerization. It may also be due to inherent nature of the polymeric material, the additives used in the polymeric material or the effect of heat on the polymeric material. The development of color is undesirable because it indicates polymer degradation and results in further reduction of the quality of the polymer. Thus, one of the objects of this invention is to provide a stabilized composition which would improve the quality of polymers by preventing the discoloration of the polymer.

Other unstable organic materials, such as synthetic lubricants, hydrocarbons, natural and synthetic rubbers, oils of animal or vegetable origin, and the like are also unstable to thermal and/or oxidative deterioration. Such materials may also be unstable to ultraviolet and/or visible light.

It is well known to stabilize polyolefins and styrenic polymers by the use of phosphites. Thus, for example, phosphites can be used in conjunction with UV absorbers such as benzophenones and benzotriazoles to achieve improved stabilization of polypropylene on outdoor exposure to sunlight. However, a phosphite is generally not used as the sole light stabilizer in polypropylene because of its limited effectiveness. Unexpectedly, it has been found that the phosphites of this invention can be used effectively in polymers, such as polypropylene, as the sole light stabilizer. Furthermore, some of the phosphites of this invention act as antioxidants for polymers, both when used alone and in combination with thiosynergists.

DETAILED DISCLOSURE

This invention accordingly relates to hindered phenyl phosphites and organic compositions stabilized therewith. More specifically, these compounds are useful as stabilizers of organic materials which are subject to thermal, oxidative and ultraviolet light degradation. The hindered phenyl phosphites of this invention have the formula

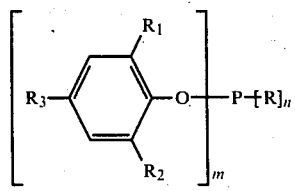

wherein $R_1$ and $R_2$ are independently lower alkyl or hydrogen, provided that only one of $R_1$ and $R_2$ is hydrogen, $R_3$ is $-(A)_q-COOR_4$ or CN where A is alkylene of 1 to 6 carbon atoms, $R_4$ is alkyl of 1 to 24 carbon atoms, phenyl or alkyl substituted phenyl, q is 0 or 1, m and n are each 1 or 2, the values of m and n being such that the trivalent state of P is satisfied, R is (a) halogen, (b) hydroxyl, provided that m is 2 and n is 1 when R is hydroxyl, (c) $-XR_5$ wherein X is S or O and $R_5$ is alkyl of 1 to 24 carbon atoms, phenyl, alkyl substituted phenyl, or when X is O is alkanoyl, benzoyl, or alkyl substituted benzoyl, (d) a group of the formula

wherein $R_6$ is phenylene, alkyl substituted phenylene or alkylene, X is as defined above, and m and n are each 1, (e) a group of the formula

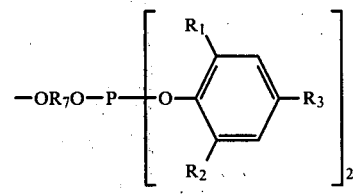

wherein $R_7$ is hydrocarbyldiacyl, $R_1$, $R_2$ and $R_3$ are as defined above, and m is 2 and n is 1, (f) A group of the formula

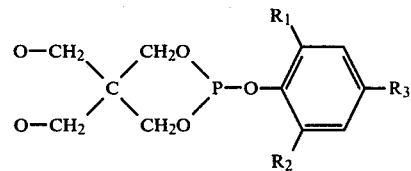

wherein $R_1$, $R_2$ and $R_3$ are as defined above, and m and n are each 1.

$R_1$ and $R_2$ are independently lower alkyl having from 1 to 12, especially 4 to 12, carbon atoms, or hydrogen, provided that only one of $R_1$ and $R_2$ is hydrogen. Preferably, one of $R_1$ and $R_2$ is a tertiary alkyl of 4 to 8 carbon atoms. Most preferably, both $R_1$ and $R_2$ are tertiary alkyl of 4 to 8 carbon atoms, as e.g., t-butyl.

Substituent $R_3$ is preferably $-COOR_4$, $-CH_2COOR_4$, $-(CH_2)_2COOR_4$ or CN. Substituent $R_4$ is preferably alkyl of 1 to 30 carbon atoms, especially 1 to 24 carbon atoms, phenyl or phenyl substituted by 1 to 3 alkyl groups of the formula

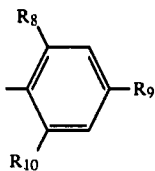

in which $R_8$, $R_9$ and $R_{10}$ independently of one another are alkyl with 1 to 18 carbon atoms or hydrogen. Examples of $R_4$ are methyl, ethyl, n-propyl, isopropyl, n-butyl, n-octyl, n-octadecyl, n-docosyl, and n-tetracosyl. Examples of $R_8$, $R_9$ and $R_{10}$ are methyl, ethyl, iso-propyl, sec-butyl, tert-butyl, sec-amyl, tert-amyl, tert-hexyl, iso-octyl, tert-octyl, sec-nonyl, tert-nonyl, sec-dodecyl, tert-dodecyl, sec-tetradecyl, sec-hexadecyl, and octadecyl.

In preferred compounds of the invention having the substituent —$XR_5$, $R_5$ is alkyl of 1 to 18 carbon atoms, phenyl, benzoyl, phenyl or benzoyl substituted by 1 or 2 alkyl groups of 1 to 18, preferably 1 to 12 carbon atoms each, and alkanoyl having 1 to 30, more preferably 1 to 22 carbon atoms.

Examples of $R_5$ as alkyl are methyl, ethyl, propyl, butyl, pentyl, hexyl, octyl, dodecyl, octadecyl, and tetracosyl. Examples of $R_5$ as alkyl substituted phenyl are methylphenyl, ethylphenyl, butylphenyl, octylphenyl, octadecylphenyl, dimethylphenyl, dibutylphenyl, dioctadecylphenyl. Examples of alkyl substituted benzoyl are 4-tertoctyl-benzoyl, 4-tert-butyl-benzoyl, and 3,4-dimethylbenzoyl. Examples of $R_5$ as alkanoyl are acetyl, propionyl, butyroyl, pelargonyl, stearoyl, caproyl, capryloyl, 2-ethylhexanoyl, lauroyl, valeroyl, palmitoyl, tridecanoyl and octanoyl.

In preferred compounds of the formula

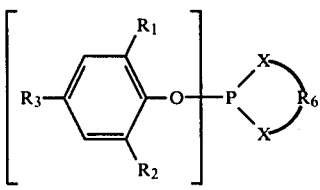

the cyclic structure

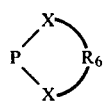

is a 5 or 6 membered ring where $R_6$ is alkylene of 2 to 24, preferably 2 to 18, carbon atoms. Examples of $R_6$ are ethylene, trimethylene, 2,2-dimethyltrimethylene, hexadecylethylene, 1,2-phenylene and alkyl substituted 1,2-phenylene where the alkyl group has 1 to 18 carbon atoms.

In preferred compounds of the formula

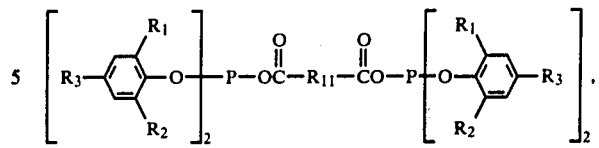

$R_{11}$ is alkylene of 1 to 34 carbon atoms, arylene or the direct bond.

Examples of $R_{11}$ as alkylene are methylene, ethylene, propylene, trimethylene, tetramethylene, hexamethylene, octamethylene, decamethylene and octadecamethylene. Examples of $R_7$ as arylene are O-, m-, or p-phenylene, and 2,3-naphthylene.

As previously stated, the compounds of the present invention are useful in the stabilization of organic material normally subject to deterioration. Organic materials such as, for example, the following polymers, can be stabilized using the compounds of the formula I.

1. Polymers which are derived from hydrocarbons with single or double unsaturation, such as polyolefins, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene-propylene copolymers, propylene-butene-1 copolymers, propylene-isobutylene copolymers, styrene-butadiene copolymers and terpolymers of ethylene and propylene with a diene, such as, for example, hexadiene, dicyclopentadiene or ethylidene-norbornene; mixtures of above mentioned homopolymers, such as for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-14-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as cross-linking agents, and also their halogen-containing modifications of low inflammability.

16. Natural polymers such as cellulose, rubber, proteins and their polymer-homologously chemically modified derivatives, such as cellulose acetates, cellulose proprionates and cellulose butyrates, or the cellulose ethers, such as methylcellulose.

17. High molecular monomeric substances, for example, mineral oils, animal and vegetable fats, oils and waxes, or oils, waxes and fats based on synthetic esters.

The compounds of this invention are particularly useful as UV light stabilizers, especially for the protection of polyolefins, for instance, polyethylene, polypropylene, poly(butene-1), poly(pentene-1), poly(3-methylbutene-1), poly(4-methylpentene-1), various ethylene-propylene copolymers and the like. The compounds of this invention are particularly useful in stabilizing polypropylene.

Other polymeric substrates in which the compounds of this invention are particularly useful are polystyrene, including impact polystyrene, ABS resin, SBR, polyisoprene, as well as natural rubber, polyesters including polyethylene terephthalate and polybutylene terephthalate, including copolymers.

The compounds of this invention are also particularly useful in stabilizing lubricating oils of various types including natural and synthetic hydrocarbon lubricating oils, particularly paraffinic lubricating oils, aliphatic esters, polyalkylene oxides, silicones, esters of phosphoric and silicic acids, highly fluorine-substituted hydrocarbons, and the like. Specifically, such aliphatic esters which are usefully stabilized comprise dihexyl acetate, di-(2-ethylhexyl)acelate, di-(3,5,5-trimethylhexyl)glutarate, di(3,5,5-trimethylpentyl)glutarate, di-(2-ethylhexyl)pimelate, di-(2-ethylhexyl)adipate, diisoamyl adipate, triamyl tricarballylate, pentaerythritol tetracaproate, dipropylene glycol dipelargonate, 1,5-pentanediol di-(2-ethylhexanoate), and the like. Other specific lubricants include polyisopropylene oxide, polyisopropylene oxide diether, polyisopropylene oxide diester, and the like, as well as methyl silicone, methylphenyl silicone, tetracosyl silicate, etc. and fluorinated oils, such as perfluorohydrocarbons.

The present invention also relates to the stabilization of fatty materials, including oils of animal or vegetable origin, which tend to deteriorate on standing on exposure to atmospheric oxygen. Also within the scope of the invention are saturated and unsaturated hydrocarbons which tend to deteriorate on storage and use, such as for example, gasolines, jet fuels, diesel mineral oils, and the like. Such hydrocarbons are protected against gum formation, discoloration and other deterioration with the stabilizers of the present invention. Greases and cutting oils may also be stabilized in the same fashion.

Fatty acids, such as stearic acid, cyclohexene and synthetic oils, such as trimethylolpropane esters of acetic acid, n-valeric acid, hexanoic acid, caprylic acid, pelargonic acid, 2-ethylhexanoic acid, 2-ethylpropanoic acid, and 2-methylpentanoic acid, and mixtures thereof are also very effectively stabilized with the foregoing stabilizers.

As previously mentioned, the stabilizers of this invention are also useful in stabilizing rubber, e.g., artificial and natural rubber. Other examples of rubber which may be stabilized according to the invention include polybutadiene rubber, polyisoprene rubber, styrene-butadiene rubber, butyl rubber, nitrile rubber, neoprene rubber and blends of artifical rubber with natural rubber, such as for example natural rubber with polybutadiene rubber. Broadly contemplated is the stabilization of any rubber normally subject to degradation.

In general, the stabilizers of this invention are employed from about 0.01 to about 5% by weight of the stabilized composition, although this will vary with the particular substrate and application. An advantageous range is from about 0.05 to about 2%, and especially 0.1 to about 1%.

The compositions are prepared by a number of means, depending on the substrate. For example, the instant stabilizers can be mixed into liquid substrates and can be milled into thermoplastic substrates. For addition to varnishes, the stabilizers can be dissolved in a co-solvent and this added to the varnish. As mentioned hereinbefore and exemplified hereinafter, levels of the stabilizers in the substrate may vary considerably depending on the particular end application, degree of protection desired, variations in the substrate, and presence of synergizing stabilizers (ultraviolet absorbers, dialkyl thiodipropionates, and the like).

Selecting the proper use level is well within the capabilities of those skilled in the art.

For addition to polymeric substrates, the stabilizers can be blended before polymerization or after polymerization, during the usual processing operations, for example, by hot-milling, the composition then being extruded, pressed, blow-molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

In the case of crosslinked polyethylene, the compounds are added before the crosslinking.

The following may be mentioned as examples of further additives with which the compounds of the formula I can be co-employed:

1. Antioxidants 1.1 Simple 2,6-dialkylphenols, such as, for example, 2,6-di-tert-butyl-4-methylphenol, 2-tert-butyl-4,6-dimethylphenol, 2,6-di-tert-butyl-4-methoxymethylphenol, 2,6-dioctadecyl-4-methylphenol.

1.2 Derivatives of alkylated hydroquinones, such as, for example, 2,5-di-tert-butyl-hydroquinone, 2,5-di-tert-amylhydroquinone, 2,6-di-tert-butyl-hydroquinone, 2,5-di-tert-butyl-4-hydroxy-anisole, 3,5-di-tert-butyl-4-hydroxy-anisole, tris-(3,5-di-tert-butyl-4-hydroxyphenyl)-phosphite, 3,5-di-tert-butyl-4-hydroxyphenyl stearate and bis(3,5-di-tert-butyl-4-hydroxyphenyl) adipate.

1.3 Hydroxylated thiodiphenyl ethers, such as, for example, 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis(3,6-di-sec-amylphenol), 4,4'-thio-bis-(6-tert-butyl-2-methylphenol) and 4,4'-bis-(2,6-dimethyl-4-hydroxyphenyl)-disulphide.

1.4 Alkylidene-bisphenols, such as, for example, 2,2'-methylene-bis-(6-tert-butyl-4-methylphenol), 2,2'-methylene-bis-(6-tert-butyl-4-ethylphenol), 4,4'-methylene-bis-(6-tert-butyl-2-methylphenol), 4,4'-methylene-bis(2,6'-di-tert-butyl-phenol), 2,6-di-(3-tert-butyl-5-methyl-2-hydroxy-benzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis(5-tert-butyl-4-hydroxy-2-methylphenyl)-butane, 2,2-bis-(5-tert-butyl-4-hydroxy-2-methylphenyl)-butane, 2,2-bis-(3,5-di-tert-butyl-4-hydroxyphenyl)-propane, 1,1,3-tris-(5-tert-butyl-4-hydroxy-2-methylphenyl)-butane, 2,2-bis-(5-tert-butyl-4-hydroxy-2-methylphenyl)-4-n-dodecylmercapto-butane, 1,1,5,5-tetra-(5-tert-butyl-4-hydroxy-2-methylphenyl)-pentane and ethylene glycol bis-[3,3-bis-(3'-tert-butyl-4'-hydroxyphenyl)-butyrate].

1.5 O—, N— and S—benzyl compounds, such as, for example, 3,5,3',5'-tetra-tert-butyl-4,4'-dihydroxydibenzyl ether, 4-hydroxy-3,5-dimethylbenzyl-mercaptoacetic acid octadecyl ester, tris(3,5-di-tert-butyl-4-hydroxybenzyl)-amine and bis-(4-tert-butyl-3-hydroxy-2,6-dimethylbenzyl)-dithioterephthalate.

1.6 Hydroxybenzylated malonic esters, such as, for example, 2,2-bis-(3,5-di-tert-butyl-2-hydroxybenzyl)-malonic acid dioctadecyl ester, 2-(3-tert-butyl-4-hydroxy-5-methylbenzyl)-malonic acid dioctadecyl ester, 2,2-bis-(3,5-di-tert-butyl-4-hydroxybenzyl)-malonic acid didodecylmercaptoethyl-ester and 2,2-bis-(3,5-di-tert-butyl-4-hydroxybenzyl)-malonic acid di-[4-(1,1,3,3-tetramethylbutyl)-phenyl]ester.

1.7 Hydroxybenzyl-aromatics, such as, for example, 1,3,5-tri-(3,5-di-tert-butyl-4-hydroxybenzyl)-2,4,6-trimethylbenzene, 1,4-di-(3,5-di-tert-butyl-4-hydroxybenzyl)-2,3,5,6-tetramethylbenzene and 2,4,6-tri-(3,5-di-tert-butyl-4-hydroxybenzyl)-phenol.

1.8 s-Triazine compounds, such as, for example, 2,4-bis-octylmercapto-6-(3,5-di-tert-butyl-4-hydroxyanilino)-s-triazine, 2-octylmercapto-4,6-bis-(3,5-di-tert-butyl-4-hydroxy-anilino)-s-triazine, 2-octylmercapto-4,6-bis-(3,5-di-tert-butyl-4-hydroxyphenoxy)-s-triazine, 2,4,6-tris-(3,5-di-tert-butyl-4-hydroxyphenoxy)-s-triazine, 2,4,6-tris-(3,5-di-tert-butyl-4-hydroxyphenylethyl)-s-triazine and 1,3,5-tris-(3,5-di-tert-butyl-4-hydroxybenzyl)-iso-cyanurate.

1.9 Amides of β-(3,5-di-tert-butyl-4-hydroxyphenyl-propionic acid such as, for example, 1,3,5-tris-(3,5-di-tert-butyl-4-hydroxyphenyl-propionyl-hexahydro-s-triazine and N,N'-di-(3,5-di-tert-butyl-4-hydroxyphenylpropionyl)-hexamethylenediamine.

1.10 Esters of β-(3,5-di-tert-butyl-4-hydroxyphenyl-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.11 Esters of β-(5-tert-butyl-4-hydroxy-3-methylphenyl propionic acid with monohydric or polyhydric alcohols, such as, for example, methanol, ethanol, octadecanol, 1,6-hexanediol 1,9-nonanediol, ethylene glycol 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]-octane.

1.12 Esters of 3,5-di-tert-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethyl hexanediol, trimethylolethane, trimethylolpropane, tris-hydroxyethyl isocyanurate and 4-hydroxymethyl-1-phospha 2,6,7-trioxabicyclo[2,2,2]octane.

1.13 Acylaminophenols, such as for example, N-(3,5-di-tert-butyl-4-hydroxyphenyl)stearic acid amide, N,N'-di-(3,5-di-tert-butyl-4-hydroxyphenyl)-thiobis-acetamide and thiophosphoric acid O,O-diethyl ester 3,5-di-tert-butyl-4-hydroxy anilide.

1.14 Benzylphosphonates, such as, for example, 3,5-di-tert-butyl-4-hydroxybenzyl-phosphonic acid dimethyl ester, 3,5-di-tert-butyl-4-hydroxybenzyl-phosphonic acid diethyl ester, 3,5-di-tert-butyl-4-hydroxybenzyl-phosphonic acid dioctadecy ester and 5-tert-butyl-4-hydroxy-3-methylbenzyl-phosphonic acid dioctadecyl ester.

1.15 Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec-butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerizes 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec-octyl-p-phenylenediamine, N-phenyl-N'-sec-octyl-p-phenylenediamine, N,N'-di-(1,4-dimethylpentyl)-p-phenylenediamine, N,N'-dimethyl-N,N'-di-(sec-octyl)-p-phenylenediamine, 2,6-dimethyl-4-methoxyaniline, 4-ethoxy-N-sec-butylaniline, the condensation produced of diphenylamine and acetone, aldol-1-naphthylamine and phenothiazine.

2. UV absorbers and light stabilizers 2.1 2-(2'-Hydroxyphenyl)-benztriazoles, such as, for example, the 5'-methyl-, 3'5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl', 3'-α-methylbenzyl-5=-methyl-, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl- derivative.

2.2 2,4-Bis-(2'-hydroxyphenyl)-6-alkyl-s-triazines, such as, for example, the 6-ethyl-, 6-heptadecyl-, or 6-undecylderivative.

2.3 2-Hydroxy-benzophenones, such as, for example, the 4-hydoxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy-derivative.

2.4 1,3-Bis-(2'-hydroxy-benzoyl)-benzenes, such as for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5 Esters of optionally substituted benzoic acids, such as, for example, phenyl salicylate, octylphenyl salicylate, dibenzoylresorcinol, bis-(4-tert.-butylbenzoyl)-resorcinol, benzoyl-resorcinol and 3,5-di-tert.-butyl-4-hydroxybenzoic acid 2,4-di-tert.-butyl-phenyl ester, octadecyl ester or 2-methyl-4,6-di-tert.-butyl-phenyl ester.

2.6 Acrylates, such as, for example, α-cyano-β, β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2methyl-indoline.

2.7 Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert-butylbenzyl-phosphonic acid monoalkyl esters, such as of the methyl, ethyl or butyl ester, nickel complexes of ketoximes such as of 2-hydroxy-4-methyl-phenyl undecyl ketonoxime, nickel 3,5-di-tert.-butyl-4-hydroxybenzoate and nickel isopropylxanthate.

2.8 Oxalic acid diamides, such as, for example, 4,4'-di-octyl-oxy-oxanilide, 2,2'-di-octyloxy-5,5'-di-tert.-butyloxanilide, 2,2'-di-dodecyloxy-5,5'-di-tert.-butyloxanilide 2-ethoxy-2'-ethyl-oxanilide, N,N'-bis-(3-dimethylaminopropyl)-oxalamide, 2-ethoxy-5-tert.-butyl-2'-ethyl-oxanilide and its mixture with 2-ethoxy-2'-ethyl-5,4'-di-tert.-butyl-oxanilide and mixtures of ortho- and para-methoxy- as well as of o- and p-ethoxy-disubstituted oxanilides.

3. Metal deactivators, such as, for example, oxanilide, isophthalic acid dihydrazide, sebacic acid bis-phenylhydrazide, bis-benzylidene-oxalic acid dihydrazide, N,N'-diacetyl-adipic acid dihydrazide, N,N'-bis-salicyloyloxalic acid dihydrazide, N,N'-bis-salicyloyl-hydrazine, N,N'-bis-(3,5-di-tert.-butyl-4-hydroxyphenyl-propionyl)-hydrazine, N-salicyloyl-N'-salicylal-hydrazine, 3-salicyloylamino-1,2,4-triazole and N,N'-bis-salicyloyl-thiopropionic acid dihydrazide.

4. Compounds which destroy peroxide, such as, for example, esters of β-thiodipropionic acid, for example the lauryl, stearyl, myristyl or tridecyl esters, mercaptobenzimidazole or the zinc salt of 2-mercapto-benzimidazole.

5. Polyamide stabilizers, such as, for example, copper salts in combination with iodides and/or phosphorus compounds and salts of divalent manganese.

6. Basic co-stabilizers, such as, for example, melamine, benzoquanamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, Zn searate, Mg stearate, Na ricinoleate and K palmitate, antimony pyrocatecholate or zinc pyrocatecholate.

7. PVC stabilizers, such as, for example, organic tin compounds, organic lead compounds and barium-cadmium salts of fatty acids.

8. Nucleating agents, such as, for example, 4-tert. butylbenzoic acid, adipic acid and diphenylacetic acid.

9. Urea derivatives, such as, for example, N-cyclohexyl-N'-1-naphthylurea, N-phenyl-N, N'-dicyclohexylura, N-phenyl-N'-2-naphthylurea, N-phenylthiourea and N,N'-dibutylthiourea.

10. Other additives, such as, for example, plasticizers, lubricants emulsifiers, fillers, carbon black, asbestos, kaolin, talc, glass fibres, pigments optical brighteners, flameproofing agents, antistatic agents, pourpoint depressants, corrosion and rust inhibitors, dispersing agents, demulsifiers, antifoaming agents, accelerators and the other chemicals used in rubber compounding, antiozonants, dyes, pigments, metal chelating agents, dyesites and the like.

The hindered phosphites of this invention are particularly useful in stabilizing polymer systems containing reinforcing agents and flame retardants, e.g., the compounds of this invention help to stabilize polyesters, e.g., polybutylene terephthalate containing fiber glass and also polyesters containing flame-retardants, e.g., polyethylene or polybutylene terephthalate containing halogenated (e.g., brominated) aryl flame-retardants.

The hindered phosphites of this invention are particularly useful in preventing discoloration due to processing as well as thermal aging and light exposure of polymer compositions containing polyacrylonitrile and polymethacrylonitrile resins. For example, a rubber modified polyacrylonitrile used for beverage bottles is inhibited from discoloration when a hindered phosphite of this invention is included in the formulation.

Often combinations such as these, particularly the sulfur-containing esters (Section 4, page 24), and/or the ultraviolet light stabilizers (Section 2, pages 21–23), will produce superior results in certain applications to those expected from the properties of the individual components.

The following formula represents co-stabilizers which are in certain instances very useful in combination with the stabilizers of this invention:

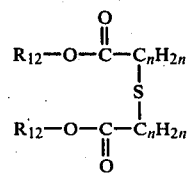

wherein $R_{12}$ is an alkyl group having from 6 to 24 carbon atoms, and n is an integer from 1 to 6. Especially useful compounds of this type are dilauryl-β-thiodipropionate (DLTDP), distearyl-β-thiodipropionate (DSTDP), and dimyristyl-β-thiodipropionate. The above co-stabilizers are used in the amount of from 0.005 to 5% by weight of the organic material, and preferably from 0.1 to 1%.

A useful co-stabilizer with which the stabilizers of this invention may be combined has the formula

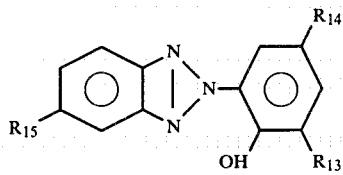

wherein
- $R_{13}$ is hydrogen, chlorine or lower alkyl containing from 1 to 6 carbon atoms,
- $R_{14}$ is hydrogen, alkyl containing 1 to 12 carbon atoms, phenyl or benzyl, and
- $R_{15}$ is hydrogen, chlorine or (lower) alkyl containing from 1 to 6 carbon atoms.

In a preferred embodiment, $R_{15}$ is hydrogen, chlorine or a methyl group; $R_{13}$ is hydrogen, chlorine, t-butyl, t-amyl; and $R_{14}$ is alkyl of from 1 to 12 carbon atoms such as methyl, ethyl, hexyl, octyl, dodecyl, t-butyl, t-amyl, isopropyl and the like.

The above benzotriazoles are added to the polymer substrate in an amount of from about 0.005% to about 5% by weight based on the weight of the polymer and more preferably from 0.05% to 2%.

Although the compounds of this invention are to some degree also effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight.

The best results have been obtained with the preferred class of thermal antioxidants, the hindered phenols. These compounds have been found to provide the best thermal stabilization with the least discoloration in the compositions of the invention. Among this preferred class of thermal antioxidants may be mentioned the following:

di-n-octadecyl(3,5-di-butyl-4-hydroxybenzyl)malonate
2,6-di-t-butylphenol
2,2'-methylene-bis(6-t-butyl-4-methylphenol)
2,6-di-t-butylhydroquinone
octadecyl-3(3,5-di-t-butyl-4-hydroxybenzylthio)acetate
1,1,3-tris-(3-t-butyl-6-methyl-4-hydroxyphenyl)butane
1,4-bis(3,5-di-t-butyl-4-hydroxybenzyl)-2,3,5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl-β-(3,5-di-t-butyl-4-hydroxyphenyl)propionate
2,4,6-tris(3,5-di-tert-butyl-4-hydroxybenzyl)-isocyanurate
di-n-dodecyl-6-tert-butyl-2,3-dimethyl-4-hydroxybenzyl phosphonate
stearamido N,N-bis-[ethylene 3-(3,5-di-t-butyl-4-hydroxyphenyl)propionate]
1,2-propylene glycol bis[3-(3,5-di-t-butyl-4-hydroxyphenyl)propionate]
pentaerythritol tetrakis-[3,5-di-t-butyl-4-hydroxyphenyl)propionate]
dioctadecyl 3,5-di-t-butyl-4-hydroxybenzylphosphonate
di-n-octadecyl 1-(3,5-di-t-butyl-4-hydroxyphenyl)ethanephosphonate The above phenolic hydrocarbon stabilizers are known and many are commercially available.

The above exemplified antioxidants and other related antioxidants which are incorporated herein by reference, are disclosed in greater detail in the following patents:

Netherlands Patent Specification No. 67/1119, issued Feb. 19, 1968; Netherlands Patent Specification No. 68/03498, issued Sept. 18, 1968; U.S. Pat. Nos. 3,255,191; 3,330,859; 3,644,482; 3,281,505; 3,531,483; 3,285,855; 3,364,250; 3,368,997; 3,357,944 and 3,758,549.

In a particularly advantageous embodiment of the invention, the hindered phosphites are employed in combination with p-hydroxybenzoates having the general formula

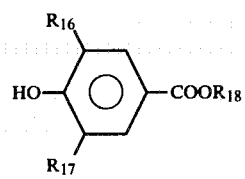

II wherein
- $R_{16}$ is (lower) alkyl containing from 1 to 6 carbon atoms,
- $R_{17}$ is hydrogen or (lower) alkyl containing from 1 to 6 carbon atoms, and
- $R_{18}$ is alkyl or alkenyl of from 1 to 24 carbon atoms, preferably alkyl of from 1 to 24 carbon atoms, phenyl, lower alkyl substituted phenyl, benzyl or lower alkyl substituted benzyl groups, such that no more than two lower alkyl substituents are present on said phenyl or benzyl groups. Preferred among the above phenyl and benzyl groups defining $R_{18}$ are phenyl and phenyl substituted by one or two alkyl groups of 1 to 12 carbon atoms.

In a preferred embodiment, $R_{16}$ and $R_{17}$ are t-butyl or t-amyl groups and $R_{18}$ is a di(lower alkyl) phenyl. Illustrative examples of hydroxybenzoates are given below:

(2',4'-di-t-butylphenyl)-3,5-di-t-butyl-4-hydroxybenzoate
methyl 3-methyl-5-isopropyl-4-hydroxybenzoate
ethyl 3,5-diisopropyl-4-hydroxybenzoate
propyl 3,5-di-sec-butyl-4-hydroxybenzoate
isobutyl 3,5-di-tert-amyl-4-hydroxybenzoate
decyl-3,5-di-tert-octyl-4-hydroxybenzoate
cyclohexyl 3,5-di-tert-amyl-4-hydroxybenzoate
dodecyl 3-methyl-5-isoamyl-4-hydroxybenzoate
octadecyl 3,5-diisopropyl-4-hydroxybenzoate
hexadecyl 3,5-di-tert-butyl-4-hydroxybenzoate
3-fluoropropyl 3,5-di-tert-amyl-4-hydroxybenzoate
allyl 3,5-di-tert-butyl-4-hydroxybenzoate
oleyl 5-methyl-5-tert-amyl-4-hydroxybenzoate
phenyl 3,5-diisopropyl-4-hydroxybenzoate p-t-octylphenyl 3,5-di-tert-amyl-4-hydroxybenzoate
(2',4'-dimethylphenyl) 3,5-di-tert-octyl-4-hydroxybenzoate
p-isopropylphenyl 3-methyl-5-tert-amyl-4-hydroxybenzoate
naphthyl 3,5-di-tert-butyl-4-hydroxybenzoate
6-methylnaphthyl 3,5-di-tert-hexyl-4-hydroxybenzoate
p-chlorophenyl 3,5-di-tert-butyl-4-hydroxybenzoate
2,4-dibromophenyl 3,5-diisopropyl-4-hydroxybenzoate The p-hydroxybenzoate light stabilizers of Formula II are added to the polymer substrate in an amount of from about 0.005% to 5% by weight based on the weight of polymer, and more preferably from 0.05% to 2%.

The compounds of this invention may be prepared by a number of methods. Method (1) can be represented by the following reaction path:

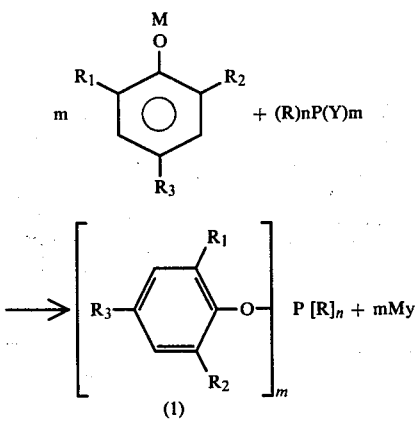

where M is an alkali metal preferably sodium or potassium or hydrogen and Y is halogen preferably bromine or chlorine, more preferably chlorine, and the other symbols are as previously defined. Where M is hydrogen, a proton acceptor, preferably a tertiary amine, such as triethylamine, is used to neutralize the acid HY which is produced as a by-product.

Method (2), illustrated below, has been found particularly advantageous in producing compounds of this invention where m=2, n=1 and R=OH, by selective hydrolysis of compounds of this invention where m=2, n=1, and —XR$_5$ is alkanoyloxy, e.g., acetoxy, as shown in the following equation:

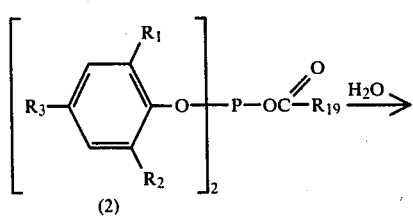

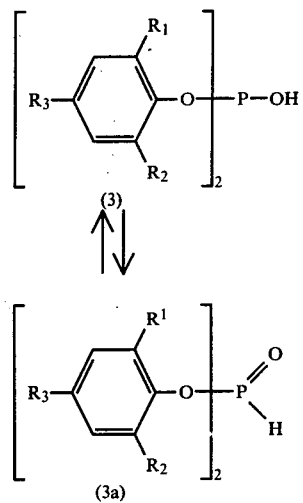

wherein R$_{19}$ is hydrogen or alkyl of 1 to 17 carbon atoms and the other symbols are as previously defined. This novel method makes possible the synthesis of stabilizers not directly accessible from the phosphorochloridite (4).

Compound (2) above can be made as follows:

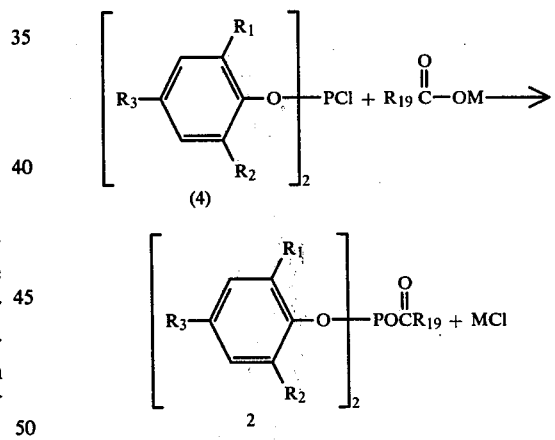

where the symbols are as previously defined.

Some of the compounds of this invention, tautomer 3 and 3a shown above, can also be made by hydrolysis or alcoholysis of the chlorodite as shown in method (3) below

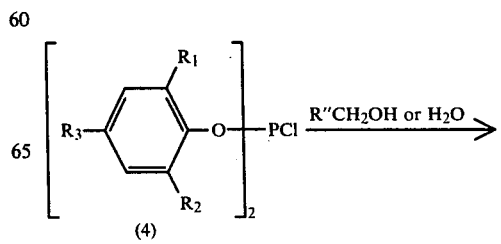

-continued

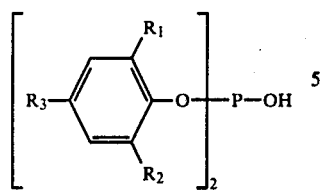

(3)

↓

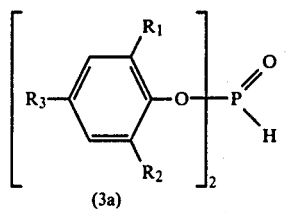

(3a)

wherein R" is alkyl, preferably of 1 to 8 carbon atoms, and the other symbols are as defined above.

The compounds of this invention of the formula

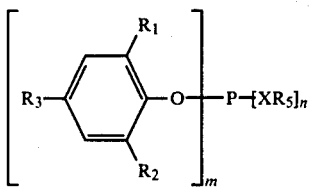

where X is O or S and $R_5$ is alkyl, phenyl, or alkyl substituted phenyl and the other symbols are as previously defined, can be made in known manner by reaction of a compound of the formula

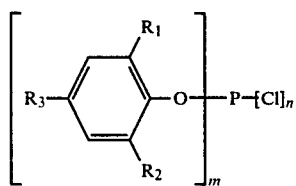

and the desired hydroxy or thiol compound, or the oxide or the thiolate.

The compounds of this invention of the formula

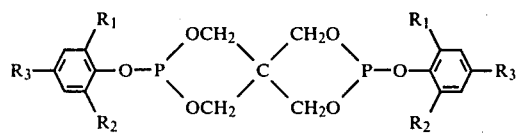

can be made in known manner by reaction of a compound of the formula

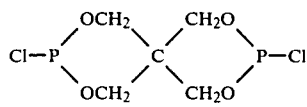

and a compound of the formula

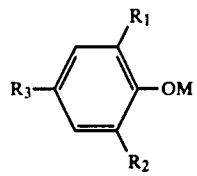

where the symbols are as previously defined. Where M is hydrogen, a proton acceptor, preferably a tertiary amine, such as triethylamine, is used to neutralize the acid HY which is produced as a by-product.

The starting materials for making the compounds of the present invention are available commercially and/or may readily be prepared by those skilled in the art from the teachings of the prior art.

The following examples, presented for illustration and not limitation, will further serve to typify the nature of the present invention. In the examples, parts are by weight, unless otherwise indicated.

EXAMPLE 1

Bis-(2,6-di-tert-butyl-4-carbomethoxy phenyl)-phosphorochloridite 27.48 grams of phosphorus trichloride was added dropwise at 24° to 30° C. over a period of 15 minutes to a solution of 105.6 grams of methyl 3,5-di-tert-butyl-4-hydroxybenzoate and 40.4 grams of triethylamine in 375 ml. of dry toluene. The turbid light-brown reaction mixture was stirred at 75° to 80° C. for three hours. The precipitated triethylamine hydrochloride was filtered and the clear filtrate concentrated to dryness at reduced pressure, the isolated residue being crystallized from toluene yielding the desired product as colorless crystals melting at 174°–176° C.

| Analysis: | % C | % H | % Cl |
|---|---|---|---|
| Calculated for $C_{32}H_{46}ClO_6P$, M.W. - 593.13 | 64.78 | 7.82 | 5.98 |
| Found | 64.68 | 7.53 | 5.58 |

EXAMPLE 2

Bis-(2,6-di-tert-butyl-4-carbo-2'4'-di-tert-butyl-phenoxyphenyl) phosphorochloridite The compound of this example was made by a similar procedure as the analogous methyl ester (Example 1) by substituting 2,4-di-tert-butylphenyl 3,5-di-tert-butyl-4-hydroxybenzoate for methyl 3,5-di-tert-butyl-4-hydroxybenzoate. The desired compound is isolated as white crystals melting at 212°–215° C.

| Analysis: | % C | % H | % Cl |
|---|---|---|---|
| Calc. for $C_{58}H_{82}ClO_6P$ M.W. - 941.67 | 73.97 | 8.77 | 3.76 |
| Found | 74.17 | 8.49 | 4.13 |

EXAMPLE 3

Bis-(2,6-di-tert-butyl-4-ethylcarbomethoxyphenyl) phosphorochloridite 20.5 grams of phosphorus trichloride was added dropwise at 30° to 38° C. over a period of 20 minutes to a solution of 87.6 grams of methyl 3-(3,5-di-tert-butyl-4-hydroxyphenyl)propionate in 117 grams of triethylamine. The reaction mixture was then heated at reflux with stirring under nitrogen for 3½ hours. 100 ml of benzene was added and heating at reflux continued for an additional 4 hours. The reaction mixture was diluted with about 300 ml of ether, washed twice with 300 ml portions of 3 N HCl and then washed thoroughly with water and finally dried over anhydrous sodium sulfate. After removal of drying agent by filtration and solvent by distillation at reduced pressures, the isolated residue was crystallized successively from n-heptane and acetonitrile yielding the desired product as white crystals melting at 93°–95° C.

| Analysis: | % C | % H | % Cl |
|---|---|---|---|
| Calc. for $C_{36}H_{54}ClO_6P$ M.W. - 649.23 | 66.61 | 8.39 | 5.46 |
| Found | 66.37 | 8.40 | 5.77 |

EXAMPLE 4

4,4 Dimethyl-2,6-dioxaphosphite of 2,4-di-tert-butylphenyl 3,5-di-tert-butyl-4-hydroxybenzoate 10.1 grams of triethylamine was added dropwise to a solution of 16.7 grams of 4,4-dimethyl-2,6-dioxa-phosphorochloridite and 43.8 grams of 2,4-di-tert-butylphenyl 3,5-di-tert-butyl-4-hydroxybenzoate dissolved in 200 ml methylene chloride at room temperature. The reaction mixture was then heated at reflux for 1 hour, cooled to room temperature, freed of precipitated triethylamine hydrochloride by filtration and finally concentrated to dryness by distillation of the solvent at reduced pressure. The residual solid was then crystallized from a solvent mixture of hexane and toluene, yielding the desired product in the form of colorless crystals melting at 196°–197°.

EXAMPLE 5

Cyclic ethylene phosphite of 2,4-di-tert-butylphenyl 3,5-di-tert-butyl-4-hydroxybenzoate 10.12 grams was added dropwise at about 25° to 40° C. to a solution of 12.6 grams of cyclic ethylene phosphorochloridite and 43.8 grams of 2,4-di-tert-butylphenyl 3,5-di-tert-butyl-4-hydroxybenzoate in 200 ml of methylene chloride. The reaction mixture was then heated at reflux for two hours, the precipitated triethylamine hydrochloride removed by filtration and the crude product isolated as a solid after removal of the solvent by distillation at reduced pressure. The crude was crystallized twice from toluene yielding the desired product as colorless crystals melting at 155°–156° C.

| Analysis: | % C | % H | % P |
|---|---|---|---|
| Calculated for $C_{31}H_{47}O_5P$ M.W. - 530.67 | 70.40 | 8.58 | 5.86 |
| Found | 70.66 | 8.89 | 5.69 |
|  | 70.40 | 8.82 |  |

EXAMPLE 6

Cyclic ethylene phosphite of n-Octyl-3,5-di-tert-butyl-4-hydroxybenzoate 18.1 grams of n-octyl 3,5-di-tert-butyl-4-hydroxybenzoate and 6.3 grams of cyclic ethylene phosphorochloridite and 5.0 grams of triethylamine are allowed to react together in 200 ml of methylene chloride while being heated at reflux for 12 hours. After cooling the reaction mixture to room temperature and washing twice with water, the organic phase was dried over sodium sulfate. The organic solution was freed of drying agent by filtration, concentrated to dryness by distillation of the solvent at reduced pressure and the recovered oil crystallized from pentane. The desired product is thus obtained as white crystals melting at 57°–58° C.

| Analysis: | % C | % H | % P |
|---|---|---|---|
| Calculated for $C_{25}H_{43}O_5P$ M.W. - 454.59 | 66.05 | 9.53 | 6.81 |
| Found | 67.07 | 9.19 | 5.87 |

Mass spectra indicates that the title compound is contaminated with a minor amount of n-octyl 3,5-di-tert-butyl-4-hydroxybenzoate. The conclusions are corroborated by IR and NMR spectra.

EXAMPLE 7

O-Acetyl-bis-(2,6-di-tert-butyl-4-carbomethoxyphenyl ester)phosphite 11.6 grams of bis-(2,6-di-tert-butyl-4-carbomethoxyphenyl)phosphorochloridite (Example 1) was dissolved in 100 ml of anhydrous methanol containing sodium acetate and the resulting solution stirred for 3 hours at room temperature. The residue, obtained as a white solid after removal of solvent by distillation at 200 mm HG and finally at 1 mm Hg., was washed with water, dried and crystallized from n-hexane. The desired product was thus obtained as white crystals melting at 130°–133° C.

| Analysis: | % C | % H | % P |
|---|---|---|---|
| Calc. for $C_{34}H_{49}O_8P$ M.W. - 616.7 | 66.21 | 8.00 | 5.02 |
| Found | 66.04 | 7.80 | 4.95 |
|  |  |  | 5.00 |

EXAMPLE 8

Bis(2,6-di-tert-butyl-4-carbomethoxyphenyl ester) phosphonic acid

A solution of 10.5 grams of O-acetyl-(2,6-di-tert-butyl-p-carbomethoxyphenyl ester)phosphite (Example 7) was dissolved in 100 ml of dioxane containing 9.0 grams of water and 1.0 gram of acetic acid and the materials heated together at reflux for 8 hours. After removal of the solvent at reduced pressures, the residue was crystallized successively from acetonitrile and ethyl acetate yielding the desired product as white crystals melting at about 211°–213° C.

| Analysis: | % C | % H |
|---|---|---|
| Calc. for $C_{32}H_{47}O_7P$ M.W. - 574.7 | 66.81 | 8.26 |
| Found | 66.43 | 7.72 |

EXAMPLE 8A

Bis(2,6-di-tert-butyl-4-carbomethoxyphenyl ester)-phosphonic acid 6.0 grams of triethylamine dissolved in 100 ml of toluene are added dropwise at 5° C. to 2.7 grams of phosphorus trichloride and 15.9 grams of methyl-3,5-di-tertiary-butyl-4-hydroxybenzoate dissolved in 50 ml of toluene and heated at reflux overnight. After cooling to room temperature and removing the triethylamine hydrochloride by filtration, the organic phase is washed three times with water, the separated organic solution is dried over sodium sulfate. After removal of the organic solvent by distillation at reduced pressure; the isolated residue is crystallized from a hexane-toluene mixture yielding the desired compound as white crystals M.P. 200°–201° C. contaminated by by-products.

EXAMPLE 9

O-Acetyl-(2,6-di-tert-butyl-4-carbo-2',4'-di-tert-butyl-phenoxyphenyl)phosphite

The compound of this example (M.P. 174°–177° C.) is prepared by an analogous method as that shown in Example 7 by substituting bis-(2,6-di-tert-butyl-4-carbo-2',4'-di-tert-butyl-phenoxyphenyl)phosphorochloridite (Example 2) for bis-(2,6-di-tert-butyl-4-carbo-methoxyphenyl)phosphorochlorodite.

EXAMPLE 10

Bis(2,6-di-tert-butyl-4-carbo-2',4'-di-tert-butylphenoxyphenyl ester)phosphonic acid The compound of this example is prepared by an analogous method as that disclosed in Example 8 by hydrolyzing the title compound of Example 9 except that p-toluene-sulfonic acid is used as catalyst. The compound of this example has a melting point of 234°–237° C.

EXAMPLE 11

O-Acetyl-(2,6-di-tert-butyl-4-ethyl-carbomethoxyphenyl)phosphite

The compound of this example (M.P. 123°–125° C.) is prepared by an analogous method to that shown in Example 7 by substituting bis(2,6-di-tert-butyl-4-carbomethoxyethylphenyl)phosphorochloridite (Example 3) for bis(2,6-di-tert-butyl-4-carbomethoxyphenyl)phosphorochlorodite.

EXAMPLE 12

Bis(2,6-di-tert-butyl-4-ethyl-carbomethoxyphenyl ester)phosphonic acid

The compound of this example is prepared by an analogous method to that disclosed in Example 8 by hydrolyzing the title compound of Example 11. The melting range observed is 105°–113° C. on crystallization from m-heptane.

EXAMPLE 13

By essentially following the procedure of Example 1 and substituting the following esters for methyl 3,5-di-tert-butyl-4-hydroxybenzoate:

(a) n-octadecyl 3-tert-butyl-4-hydroxybenzoate
(b) n-dodecyl 3-methyl-5-tert-butyl-4-hydroxybenzoate
(c) n-hexyl 3,5-di-isopropyl-4-hydroxybenzoate there are respectively obtained:

(a) bis-(2-tert-butyl-4-carbo-n-octadecyloxyphenyl)-phosphorochloridite.
(b) bis-(2-methyl-5-tert-butyl-4-carbo-n-dodecyloxyphenyl)phosphorochloridite.
(c) bis-(2,6-di-isopropyl-4-carbo-n-hexoxyphenyl)phosphorochloridite.

EXAMPLE 14

By essentially following the procedure of Example 2 and substituting the following esters for 2',4'-di-tert-butylphenyl 3,5-di-tert-butyl-4-hydroxybenzoate:

(a) 2'-methyl-4',6'-di-tert-butylphenyl 3,5-di-tert-butyl-4-hydroxybenzoate
(b) 2',6'-di-sec.-butyl-4'-methylphenyl 3,5-di-tert-butyl-4-hydroxybenzoate
(c) 2',4',6'-tri-isopropylphenyl 3,5-di-tert-butyl-4-hydroxybenzoate
(d) 2',4',6'-tri-tert-butylphenyl 3,5-di-tert-butyl-4-hydroxybenzoate
(e) 4'-n-dodecyl-2',6'-dimethylphenyl 3,5-di-tert-butyl-4-hydroxybenzoate there are respectively obtained:

(a) bis-(2,6-di-tert-butyl-4-carbo-2'-methyl-4',6'-di-tert-butylphenoxyphenyl)phosphorochloridite.
(b) bis-(2,6-di-tert-butyl-4-carbo-2',6'-di-sec.-butyl-4'-methylphenoxyphenyl)phosphorochloridite
(c) bis-(2,6-di-tert-butyl-4-carbo-2',4',6'-triisopropylphenoxyphenyl)phosphorochloridite
(d) bis-(2,6-di-tert-butyl-4-carbo-2',4',6'-tri-tert-butylphenoxyphenyl)phosphorochloridite.
(e) bis-(2,6-di-tert-butyl-4-carbo-2',6'-di-methyl-4'-n-dodecylphenoxyphenyl)phosphorochloridite.

EXAMPLE 15

By essentially following the procedure of Example 3 and substituting the following esters for methyl-3-(3,5-di-tert-butyl-4-hydroxyphenyl)propionate:

(a) n-octadecyl 6-(3,5-di-tert-butyl-4-hydroxyphenyl)-hexanoate.
(b) n-tetracosyl 3-(3,5-di-tert-butyl-4-hydroxyphenyl)-propionate
(c) n-octyl 3,5-di-tert-butyl-4-hydroxyphenylacetate there are respectively obtained:

(a) bis-(2,6-di-tert-butyl-4-n-pentylcarbo-n-octadecyloxyphenyl)phosphorochloridite
(b) bis-(2,6-di-tert-butyl-4-ethyl-carbo-n-tetracosyloxyphenyl)phosphorochloridite
(c) bis-(2,6-di-tert-butyl-4-methyl-carbo-n-octyloxyphenyl)phosphorochloridite.

EXAMPLE 16

By essentially following the procedure of Example 5 and substituting the following phosphorochloridites for cyclic ethylene phosphorochloridite of (a) 2-Chloro-1,3,2-benzodithiaphosphole
(b) 2-Chloro-1,3,2-benzodioxaphosphole
(c) ethylene phosphorochloridothioate there are obtained the corresponding cyclic phosphites of 2,4-di-tert-butyl 3,5-di-tert-butyl-4-hydroxybenzoate.

EXAMPLE 16A

In a similar manner to Example 16 there are obtained the corresponding cyclic phosphites by reaction of each of (a) cyclic ethylene ester of phosphorochloridous acid and
(b) cyclic 2,2-dimethyltrimethylene ester of phosphorochloridous acid with each of the following:
(c) methyl 3,5-di-tert-butyl-4-hydroxybenzoate
(d) octadecyl 3,5-di-tert-butyl-4-hydroxybenzoate
(e) methyl 3-(3-tert-butyl-5-methyl-4-hydroxyphenyl)-phosphonate
(f) n-octyl (3,5-di-tert-butyl-4-hydroxyphenyl)acetate
(g) n-octadecyl 3-(3,5-di-tert-butyl-4-hydroxyphenyl)-propionate

EXAMPLE 17

By essentially following the procedure of Example 7 and substituting the following salts for sodium acetate:

(a) sodium benzoate
(b) sodium propionate
(c) sodium stearate there are respectively obtained:

(a) O-benzoyl-bis(2,6-di-tert-butyl-p-carbomethoxyphenyl)phosphite
(b) O-propionyl-bis(2,6-di-tert-butyl-p-carbomethoxyphenyl)phosphite
(c) O-stearyl-bis(2,6-di-tert-butyl-p-carbomethoxyphenyl)phosphite

EXAMPLE 18

Bis-(2,6-di-tert-butyl-4-carbo-n-octadecyloxyphenyl)-phosphorochloridite

The compound of this example was made in a similar manner to that of Example 1 by reacting phosphorus trichloride with n-octadecyl-3,5-di-tert-butyl-4-hydroxybenzoate employing triethylamine as acid acceptor. The product was isolated as a waxy white solid.

| Analysis: | % Cl |
|---|---|
| Calc. | 3.31 |
| Found | 2.82 |

EXAMPLE 19

O-Acetyl-bis(2,6-di-tert-butyl-4-carbo-n-octadecyloxyphenyl)phosphite

The compound of this example was made in a similar manner to that of Example 7 by reacting the compound of Example 18 with sodium acetate dissolved in a solvent mixture of methanol and benzene. The compound of this example melts at 70°–75° C. after successive crystallization from ethyl acetate and isopropanol.

EXAMPLE 20

Bis(2,6-di-tert-butyl-4-carbo-n-octadecyloxyphenyl ester)phosphonic acid

The compound of this example was made in a similar manner to that of Example 8 by hydrolyzing the compound of Example 19 in a water-dioxane medium at reflux (95°–96° C.) in the presence of a cataytic amount of p-toluenesulfonic acid. The compound of this example is isolated as white crystals melting at 114°–116° after crystallization from methyl ethyl ketone.

| Analysis: | % C | % H |
|---|---|---|
| Calc. | 75.38 | 11.02 |
| Found | 75.17 | 11.14 |

EXAMPLE 21

Bis-(2,6-di-tert-butyl-4-ethylcarbo-n-octadecyloxyphenyl)phosphorochloridite

The compound of this example was made in a similar manner to that of Example 3 by reacting n-octadecyl 3-(3,5-di-tert-butyl-4-hydroxyphenyl)-propionate with phosphorus trichloride in triethylamine. The product was isolated as a white waxy solid. Infrared absorption spectrum conformed to the structure of this product.

EXAMPLE 22

O-Acetyl-bis(2,6-di-tert-butyl-4-ethylcarbo-n-octadecyloxyphenyl)phosphite

A. The compound of this example (M.P. 44°–47°) was prepared by an analogous method to that disclosed in Example 7 by reacting the compound of Example 21 with sodium acetate dissolved in methanol.

B. By following the above procedure (A) and employing the appropriate phosphorochloridite starting compounds the following compounds are prepared:

(a) O-acetyl-bis(2-tert-butyl-4-carbo-n-octadecyloxyphenyl)phosphite
(b) O-acetyl-bis(2,6-di-isopropyl-4-carbo-n-hexoxyphenyl)phosphite
(c) O-acetyl-bis(2,6-di-tert-butyl-4-carbo-2',4'6'-tri-isopropylphenoxyphenyl)phosphite
(d) O-acetyl-bis(2,6-di-tert-butyl-4-carbo-2',4',6'-tri-tert-butylphenoxyphenyl)phosphite
(e) O-acetyl-bis(2,6-di-tert-butyl-4-n-pentyl-carbo-n-octadecyloxyphenyl)phosphite
(f) O-acetyl-bis(2,6-di-tert-butyl-4-methyl-carbo-n-octyloxyphenyl)phosphite

EXAMPLE 23

Bis(2,6-di-tert-butyl-4-ethylcarbo-n-octadecyloxyphenyl ester)phosphonic acid

A. The compound of this example was prepared by an analogous method to that disclosed in Example 8 by hydrolyzing the compound of Example 22 in aqueous dioxane at reflux (Ca. 96°) using p-toluene sulfonic acid as catalyst. The compound melts at 72°–75° C. after being purifified by dry-column chromatography using silica-gel.

| Analysis: | % C | % H |
|---|---|---|
| Calc. | 75.90 | 11.19 |
| Found | 75.87 | 10.88 |

B. By following the above procedure (A) and employing the appropriate o-acetyl bis-phosphite starting compounds listed in Example 22(B) the following compounds are prepared:

(a) bis(2-tert-butyl-4-carbo-n-octadecyloxyphenyl ester)phosphonic acid
(b) bis(2,6-di-isopropyl-4-carbo-n-hexoxyphenyl ester)phosphonic acid
(c) bis(2,6-di-tert-butyl-4-carbo-2',4',6'-tri-isopropylphenoxyphenyl ester)phosphonic acid
(d) bis(2,6-di-tert-butyl-4-carbo-2',4',6'-tri-tert-butylphenoxyphenyl ester)phosphonic acid
(e) bis(2,6-di-tert-butyl-4-n-pentyl-carbo-n-octadecyloxyphenyl ester)phosphonic acid
(f) bis(2,6-di-tert-butyl-4-methyl-carbo-n-octyloxyphenyl ester)phosphonic acid.

EXAMPLE 24

1,000 parts of polypropylene powder (Moplen Fiber Grade) powder [melt index 20 (230° C., 2,160 g)] are mixed in a Brabender kneader at 200° C. with 2 parts of β-(3,5-di-tert-butyl-4-hydroxyphenyl)propionic acid octadecyl ester and 2.5 parts of the light stabilizer of the invention.

The mixture homogenised in this way is withdrawn from the kneader and is pre-pressed, by means of a toggle press, into sheets 2–3 mm thick which are then converted at 260° C. in a heated platen press by means of suitable matrices, first into films 0.3 mm thick and, in a further process step, into films 0.1 mm thick.

The films thus produced are heat-treated for 1 hour at 150° C., while avoiding cooling below 150° C., and, directly afterwards, are chilled in water at 15° C. The films produced in this way have a homogeneous structure of fine spherulites. Test pieces punched from them have an elongation of approx. 800%.

The films without light stabilizer which were used as a comparison are produced in the same manner.

The polypropylene films are mounted on sample carriers and exposed in a Xeno-150 testing apparatus. After varying periods of time, pieces of film are withdrawn, 5 test pieces are punched from each in the form of tensile test bars and the residual elongation of the latter is determined. The time of exposure, after which the elongation at break of the films has declined to 50% of its value before exposure, is taken as a measure of the protective action of the light stabilizer. The value obtained are listed in the tables which follow.

Table Ia

| LIGHT STABILIZATION DATA IN POLYPROPYLENE | |
|---|---|
| Stabilizer* | Hours of exposure in the Xeno apparatus when the elongation at break has declined to 50% of the initial value |
| cyclic ethylene phosphite of 2,4-di-tert-butylphenyl 3,5-di-tert-butyl-4-hydroxybenzoate | 4310 |
| 4,4-dimethyl-2,6-dioxaphosphite of 2,4-di-tert-butylphenyl-3,5-di-tert-butyl-4-hydroxybenzoate | 2560 |
| None | 800 |

Table Ib

| Stabilizer* | Hours of exposure in the Xeno apparatus when the elongation at break has declined to 50% of the initial value |
|---|---|
| cyclic ethylene phosphite of n-octyl 3,5-di-tert-butyl-4-hydroxybenzoate | 4340 |

Table Ib-continued

| Stabilizer* | Hours of exposure in the Xeno apparatus when the elongation at break has declined to 50% of the initial value |
|---|---|
| bis(2,6-di-tert-butyl-p-carbomethoxy phenyl ester) phosphonic acid | 5198 |
| None | 1040 |

*0.25% of the indicated stabilizer is present in the above formulations. Each formulation and the blank also contain 0.2% octadecyl 3-(3',5'-di-t-butyl-4'-hydroxyphenol)propionate.

Comparatively good stabilization is obtained when the concentration of hindered phosphite varies from 0.05% to 1%.

Other hindered phenolic antioxidants may be used in place of octadecyl 3-(3',5'-di-t-butyl-4'-hydroxyphenyl) propionate in the above mentioned compositions with hindered phosphites as, for example, di-n-octadecyl α-(3-t-butyl-4-hydroxy-4-methylbenzyl)malonate, 2,4-bis(n-octylthio)-6-(3,4-di-t-butyl-4-hydroxyaniline)-1,3,5-triazine, tetrakis-[methylene-3-(3',5'-di-tert-butyl-4'-hydroxyphenyl)propionate]methane, di-octadecyl(3,5-di-t-butyl-4-hydroxybenzyl)phosphonate, tris-(3,5-di-t-butyl-4-hydroxybenzyl) isocyanurate, 26,-di-tert-butyl-4-methylphenol, N,N,N-tris-(3,5-di-tert-butyl-4-hydroxybenzyl)isocyanurate, and 2,4,6-tris(3,5-di-tert-butyl-4-hydroxybenzyl)-1,3,5-trimethylbenzene.

The hindered phosphite compositions of the above tables are also stabilized when the following UV absorbers are added to the compositions:

(a) 2-hydroxy-4-methoxy-5-sulfobenzophenone trihydrate
(b) 2-hydroxy-4-n-octoxybenzophenone
(c) 2,2'-thiobis(4-t-octylphenolate)-1-n-butylamine nickel II
(d) p-octylphenyl salicylate
(e) 2,2'-dihydroxy-4,4'-dimethoxybenzophenone
(f) 2(2'-hydroxy-5'-methylphenyl)-benzotriazole
(g) 2(2'-hydroxy-3',5'-di-t-butylphenyl)-5-chlorobenzotriazole.

The compositions of the above tables are also stabilized when the indicated phosphites are replaced with the following stabilizers:

(a) O-acetyl-bis-(2,6-di-tert-butyl-4-carbomethoxyphenyl ester)phosphite
(b) bis(2,6-di-tert-butyl-4-carbomethoxyphenyl ester)phosphonic acid
(c) bis(2,6-di-tert-butyl-4-carbo-2',4'-di-tert-butylphenoxyphenyl ester)phosphonic acid
(d) O-acetyl-(2,6-di-tert-butyl-4-carbo-2',4'-di-tert-butylphenoxyphenyl)phosphite
(e) bis(2,6-di-tert-butyl-4-ethyl-carbomethoxyphenyl ester)phosphonic acid
(f) bis-(2,6-di-tert-butyl-4-carbomethoxyphenyl) phosphorochloridite
(g) O-acetyl-(2,6-di-tert-butyl-4-ethylcarbomethoxyphenyl)phosphite
(h) bis-(2,6-di-tert-butyl-4-carbo-n-octadecyloxyphenyl ester)phosphonic acid
(i) bis-(2,6-di-tert-butyl-4-ethylcarbo-n-octadecyloxyphenyl ester)phosphonic acid.

EXAMPLE 25

High impact polystyrene resin containing elastomer (i.e., butadiene-styrene) is stabilized against loss of elongation properties due to exposure to ultraviolet light by incorporation of 0.2% by weight of 4,4-dimethyl-2,6-dioxaphosphite of 2,4-di-tert-butylphenyl 3,5-di-tert-butyl-4-hydroxybenzoate.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C. and a pressure of 2,000 pounds per square inch into sheet of uniform thickness (25 mil). The sheets are then cut into strips approximately 4×0.5 inches. A portion of these strips is then measured for percent of elongation in the Instron Tensile Testing Apparatus (Instron Engineering Corporation, Quincy, Mass.). The remaining portions of the strips are placed in an FS/BL chamber where the samples are mounted on white cardboard stock and the time to 50% reduction in elongation is measured. The stabilized polystyrene resin retains its elongation property longer than the unstabilized resin.

EXAMPLE 26

Unstabilized linear polyethylene is solvent blended in methylene chloride with 0.5% by weight of the substrate of O-acetyl-bis(2,6-di-tert-butyl-p-carbomethoxyphenyl ester)phosphite and then vacuum dried. The resin is then extrusion compounded on a 1 inch 24/1=L/D extruder, melt temperature 450° F. (232° C.) and pressed for 7 minutes at a temperature of 163° C. and a pressure of 2,000 psi into a sheet of uniform thickness of 100 ml. The sheets are then cut into plaques of 2 inch×2 inch. The plaques are then exposed in an FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant.

EXAMPLE 27

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5 N NaOH solution.

To the emulsion is added 50 ml of 25% NaCL solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (>1 mm) at 40°-45° C.

The dried rubber (25 g) is heated under nitrogen at 125° C. in a Brabender mixer and to this is added with mixing 0.25 g (0.5%) of the cyclic ethylene phosphite of 2,4-di-tert-butylphenyl 3,5-di-tert-butyl-4-hydroxybenzoate. The composition is mixed for 5 minutes after which it is cooled and compression molded at 125° C. into 5"×0.025" plaques.

The plaques are exposed to an Xenon Arc weatherometer and the color measurement (L-b) is made after 45, 125 and 290 hours. The samples stabilized with the above compound are found to be much more light stable than the unstabilized samples.

EXAMPLE 28

Unstabilized thoroughly dried polyethylene terphthalate chips are dry blended with 1.0% of bis(2,6-di-tert-butyl-p-carbomethoxyphenyl ester)phosphonic acid. 60/10 denier multifilament is melt spun at a melt temperature of 290° C. The oriented fiber is wound on white cards and exposed in an Xenon Arc Fadeometer. Color measurements are made periodically with a Hunter Color Difference Meter Model D25. The stabilized samples are found to be much more light stable than the unstabilized samples.

EXAMPLE 29

(a) A composition comprising acrylonitrile-butadiene-styrene terpolymer and 1% by weight of bis(2,6-di-tert-butyl-4-carbo-2',4'-di-tert-butylphenoxyphenyl ester)phosphonic acid resists embrittlement due to exposure to ultraviolet light longer than one which does not contain the stabilizer.

(b) A composition comprising polyurethane prepared from toluene diisocyanate and alkylene polyols and 1.0% by weight of O-acetyl-(2,6-di-tert-butyl-4-carbo-2',4'-di-tert-butylphenoxyphenyl)phosphite is more stable to sunlight, fluorescent sunlamps, black lights and fluorescent lights than the unformulated polyurethane.

(c) A composition comprising a polycarbonate prepared from bisphenol-A and phosgene and 1% by weight of bis(2,6-di-tert-butyl-4-carbo-2',4'-di-tert-butylphenoxyphenyl ester)phosphonic acid resists discoloration due to exposure to ultraviolet light longer than one which does not contain the stabilizer.

(d) A composition comprising polymethylmethacrylate and 0.25% by weight of bis(2,6-di-tert-butyl-4-carbo-2',4'-di-tert-butylphenoxyphenyl ester)phosphonic acid resists discoloration due to exposure to ultraviolet light longer than one which does not contain the stabilizer.

EXAMPLE 30

(a) A stabilized polyamide (nylon 6,6) is prepared by incorporating therein 0.1% of bis(2,6-di-tert-butyl-p-carbomethoxyphenyl ester)phosphonic acid. The light stability of the stabilized composition is superior to that of an unstabilized polyamide.

(b) A stabilized polyphenylene oxide polymer (prepared by polymerizing 2,6-dimethylphenol is prepared by incorporating therein 0.5% by weight of the cyclic ethylene phosphite of n-octyl-3,5-di-tert-butyl-4-hydroxybenzoate. The stabilized compositions resist embrittlement due to exposure to ultraviolet light longer than one which does not contain the stabilizer.

(c) A stabilized crystalline polystyrene is prepared by incorporating therein 0.1% weight of the cyclic ethylene phosphite of 3,5-di-tert-butyl-4-hydroxybenzonitrile. The stabilized composition resists embrittlement due to exposure to ultraviolet light longer than one which does not contain the stabilizer.

Antioxidants may also be incorporated into each of the above mentioned compositions, for example, di-n-octadecyl-α,α'-bis(3-t-butyl-4-hydroxy-5-methylbenzyl) malonate, 2,4-bis(4-hydroxy-3,5-di-t-butylphenoxy)-6-(n-octylthioethylthio)-1,3,5-triazine, 2,4-bis(3,5-di-t-butyl-hydroxyphenoxy)-6-(n-octylthio-1,3,5-triazine, di-n-octadecyl 3(3',5'-di-t-butyl-4-hydroxyphenyl)propionate, respectively.

EXAMPLE 31

Method of Testing Antioxidants in Polypropylene

Unstabilized polypropylene powder (Hercules Profax 6501) was thoroughly blended with the indicated amounts of additives. The blended materials were then milled on a two-roll mill at 182° C. for 5 minutes, after which time the stabilized polypropylene was sheeted from the mill and allowed to cool.

The milled polypropylene sheets were then cut into pieces and compression molded on a hydraulic press at 220° C., 175 psi into 25 mil thick plaques.

Testing Method: Rotary Oven-Aging Test

The resulting plaques of 25 mil thickness were tested for resistance to accelerated aging in a rotary oven at 150° C. When the plaques showed the first signs of decomposition (e.g., cracking or brown edges) they were considered to have failed. The results are shown below in the table. The amounts of the additives are expressed in weight percent based on the weight of the polymer.

TABLE 2

Stabilizing Effectiveness of Bis-(2,6-di-tert-butyl-4-ethylcarbo-n-octadecyloxyphenyl ester)phosphonic acid (Ex. 23) in Polypropylene 6501

| Formulations | Time to Failure Hrs. |
| --- | --- |
| Blank | 3 |
| 0.3% Bis-(2,6-di-tert-butyl-4-ethylcarbo-n-octadecyloxyphenyl ester)phosphonic acid | 250 |
| 0.3% DSTDP | 100 |
| 0.1% (Bis-(2,6-di-tert-butyl-4-ethylcarbo-n-octadecyloxyphenyl ester)phosphonic acid + 0.3% DSTDP | 400 |

The results of Table show that the compound is an effective antioxidant for polypropylene alone and with distearylthiodipropionate (DSTDP).

What is claimed is:

1. A compound of the formula

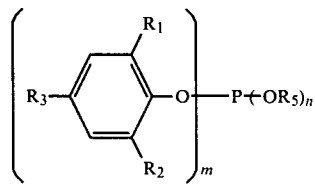

wherein $R_1$ and $R_2$ are independently lower alkyl or hydrogen, provided that only one of $R_1$ and $R_2$ is hydrogen, $R_3$ is —(A)—COOR$_4$ or CN where A is alkylene of 1 to 24 carbon atoms, $R_4$ is alkyl of 1 to 24 carbon atoms, phenyl or alkyl substituted phenyl q is 0 or 1 m and n are each 1 or 2, the values of m and n being such that the trivalent state of is satisfied, and $R_5$ is alkanoyl, benzoyl, or alkyl substituted benzoyl.

2. A compound according to claim 1 wherein $R_1$ and $R_2$ are independently alkyl having 4 to 12 carbon atoms, $R_3$ is a group selected from —COOR$_4$, —CH$_2$COOR$_4$, —(CH$_2$)$_2$COOR$_4$ or —CN, $R_4$ is alkyl of 1 to 24 carbon atoms, phenyl or phenyl substituted by 1 to 3 alkyl groups each having 1 to 18 carbon atoms, and R, m and n are as defined in claim 1.

3. A compound according to claim 2 wherein $R_1$ and $R_2$ are tert-butyl groups and R is hydroxyl.

4. A compound according to claim 2 wherein $R_1$ and $R_2$ are tert-butyl groups, and $R_5$ is benzoyl, or alkanoyl of 1-22 carbon atoms.

5. A compound according to claim 1 which is O-acetyl-bis(2,6-di-tert-butyl-p-carbomethoxyphenyl ester)-phosphite.

6. A compound according to claim 1 which is O-acetyl-bis(2,6-di-tert-butyl-4-carbo-2',4'-di-tert-butyl phenoxyphenyl)phosphite.

7. A compound according to claim 1 which is O-acetyl-(2,6-di-tert-butyl-4-ethylcarbomethoxyphenyl)-phosphite.

8. A compound according to claim 1 which is O-acetyl-bis(2,6-di-tert-butyl-4-carbo-n-octadecyloxyphenyl)-phosphite.

9. A compound according to claim 1 which is O-acetyl-bis(2,6-di-tert-butyl-4-ethylcarbo-n-octadecyloxyphenyl)phosphite.

10. A composition of matter comprising an organic polymeric synthetic material normally subject to thermal, oxidative and ultraviolet degradation and stabilized with (a) 0.005% to 5% of a stabilizing compound according to claim 1, (b) 0 to 5% of a phenolic antioxidant, (c) 0 to 5% of a thio co-stabilizer, (d) 0 to 5% of a UV absorber, and (e) 0 to 5% of a light stabilizer.

11. A composition according to claim 10 wherein the organic material is a polyolefin.

12. A composition according to claim 10 wherein the organic material is polypropylene.

13. A composition according to claim 10 wherein the stabilizing compound (a) is the sole light stabilizer, the concentrations of the UV absorber of (d) and the light stabilizer of (e) being equal to 0.

14. The composition according to claim 10 consisting essentially of (i) polyolefin, (ii) a stabilizing compound (a), and (iii) 0.005 to 5% of a phenolic antioxidant selected from tetrakis[methylene 3-(3',5'-di-tert-butyl-4'-hydroxyphenyl)propionate]methane, octadecyl 3-(3',5'-di-tert-butyl-4'-hydroxyphenyl)propionate, di-n-octadecyl-3,5-di-tert-butyl-4-hydroxybenzyl phosphonate, 2,6-di-t-butyl-4-methylphenol, and tris-2,4,6-(3,5-di-t-butyl-4-hydroxybenzyl)isocyanurate.

15. A composition according to claim 10 wherein the stabilizing compound (a) is the sole antioxidant and where (b) is equal to 0.

* * * * *